(12) United States Patent
Keating et al.

(10) Patent No.: US 11,571,553 B2
(45) Date of Patent: Feb. 7, 2023

(54) BALLOON GUIDE CATHETER WITH THERMALLY EXPANDABLE MATERIAL

(71) Applicant: Neuravi Limited, Galway (IE)

(72) Inventors: Karl Keating, Galway (IE); Ronald Kelly, Cannistown (IE)

(73) Assignee: Neuravi Limited, Galway (IE)

( * ) Notice: Subject to any disclaimer, the term of this patent is extended or adjusted under 35 U.S.C. 154(b) by 444 days.

(21) Appl. No.: 16/601,202

(22) Filed: Oct. 14, 2019

(65) Prior Publication Data

US 2020/0353226 A1    Nov. 12, 2020

Related U.S. Application Data

(60) Provisional application No. 62/845,683, filed on May 9, 2019, provisional application No. 62/845,699, filed on May 9, 2019, provisional application No. 62/845,747, filed on May 9, 2019, provisional application No. 62/845,711, filed on May 9, 2019.

(51) Int. Cl.
*A61M 25/10* (2013.01)
*A61F 2/958* (2013.01)

(52) U.S. Cl.
CPC ............. *A61M 25/10* (2013.01); *A61F 2/958* (2013.01); *A61F 2002/9586* (2013.01); *A61M 2205/02* (2013.01)

(58) Field of Classification Search
CPC ...... A61B 17/12136; A61F 2002/9586; A61M 25/10; A61M 29/02; A61K 49/0091
See application file for complete search history.

(56) References Cited

U.S. PATENT DOCUMENTS

| | | |
|---|---|---|
| 4,323,071 A | 4/1982 | Simpson et al. |
| 4,684,363 A | 8/1987 | Ari et al. |
| 4,715,378 A | 12/1987 | Pope, Jr. et al. |
| 4,753,238 A | 6/1988 | Gaiser |
| 4,793,351 A | 12/1988 | Landman et al. |
| 4,811,737 A | 3/1989 | Rydell |
| 4,821,722 A | 4/1989 | Miller et al. |
| 5,035,705 A | 7/1991 | Burns |

(Continued)

FOREIGN PATENT DOCUMENTS

| | | |
|---|---|---|
| JP | 2016168151 | 9/2016 |
| WO | 2007139799 | 12/2007 |

(Continued)

OTHER PUBLICATIONS

Co-Pending, co-owned, U.S. Appl. No. 16/601,256, filed Oct. 14, 2019.

(Continued)

*Primary Examiner* — Deanna K Hall
(74) *Attorney, Agent, or Firm* — Cohen & Hildebrand, PLLC

(57) ABSTRACT

A balloon catheter including a heating element disposed about a portion of an outer surface of a catheter shaft; a balloon mounted about the outer surface of the catheter shaft to coincide with the heating element; and thermally expandable material disposed inside the mounted balloon. The balloon catheter eliminating the need for pressurized liquid inflation media to be dispensed into/expelled from the balloon in order to inflate/deflate, respectively, the balloon.

19 Claims, 3 Drawing Sheets

(56) References Cited

U.S. PATENT DOCUMENTS

| | | |
|---|---|---|
| 5,100,385 A | 3/1992 | Bromander |
| 5,135,486 A | 8/1992 | Eberle et al. |
| 5,224,933 A | 7/1993 | Bromander |
| 5,256,143 A | 10/1993 | Miller et al. |
| 5,800,421 A | 9/1998 | Lemelson |
| 6,102,891 A | 8/2000 | Maria van Erp |
| 6,102,931 A | 8/2000 | Thornton |
| 6,709,429 B1 | 3/2004 | Schaefer et al. |
| 6,811,559 B2 | 11/2004 | Thornton |
| 6,953,431 B2 | 10/2005 | Barthel |
| 6,994,687 B1 | 2/2006 | Shkolnik |
| 7,160,266 B2 | 1/2007 | Shkolnik |
| 7,338,511 B2 * | 3/2008 | Mirigian .......... A61B 17/12113 606/200 |
| 7,678,075 B2 | 3/2010 | Wantink et al. |
| 8,298,218 B2 * | 10/2012 | Mahrouche ............ A61B 18/02 606/192 |
| 8,926,560 B2 | 1/2015 | Dinh et al. |
| 9,155,869 B2 | 10/2015 | Ehrenreich et al. |
| 9,463,035 B1 | 10/2016 | Greenhalgh et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,682,152 B2 | 6/2020 | Vale et al. |
| 11,202,891 B2 | 12/2021 | Gulachenski et al. |
| 2003/0023204 A1 | 1/2003 | Vo et al. |
| 2004/0260329 A1 | 12/2004 | Gribbons et al. |
| 2005/0070881 A1 | 3/2005 | Gribbons et al. |
| 2005/0124932 A1 | 6/2005 | Foster et al. |
| 2005/0182359 A1 | 8/2005 | Chin et al. |
| 2006/0030814 A1 | 2/2006 | Valencia et al. |
| 2008/0200904 A1 | 8/2008 | Cluff et al. |
| 2012/0265134 A1 | 10/2012 | Echarri et al. |
| 2013/0289549 A1 | 10/2013 | Nash et al. |
| 2014/0188043 A1 | 7/2014 | Shibahara |
| 2014/0257359 A1 | 9/2014 | Fegels et al. |
| 2015/0174363 A1 | 6/2015 | Sutermeister et al. |
| 2015/0224290 A1 | 8/2015 | Chanduszko et al. |
| 2016/0001040 A1 | 1/2016 | Yamaguchi et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |

(56)     References Cited

U.S. PATENT DOCUMENTS

| | | |
|---|---|---|
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0333192 A1 | 11/2018 | Sliwa et al. |
| 2019/0167287 A1 | 6/2019 | Vale et al. |
| 2019/0359786 A1* | 11/2019 | Trahan .................... B01F 27/82 |
| 2020/0246036 A1 | 8/2020 | Kallmes et al. |
| 2022/0143360 A1 | 5/2022 | Kugler et al. |

FOREIGN PATENT DOCUMENTS

| | | |
|---|---|---|
| WO | 2013163254 | 10/2013 |
| WO | 2017192999 | 11/2017 |

OTHER PUBLICATIONS

Co-Pending, co-owned, U.S. Appl. No. 16/601,185, filed Oct. 14, 2019.

Co-Pending, co-owned, U.S. Appl. No. 16/601,221, filed Oct. 14, 2019.

L.E. Romans, "The Use of Contrast Media in the CT Department", CEWebsource.com, May 15, 2013 (50 pp).

* cited by examiner

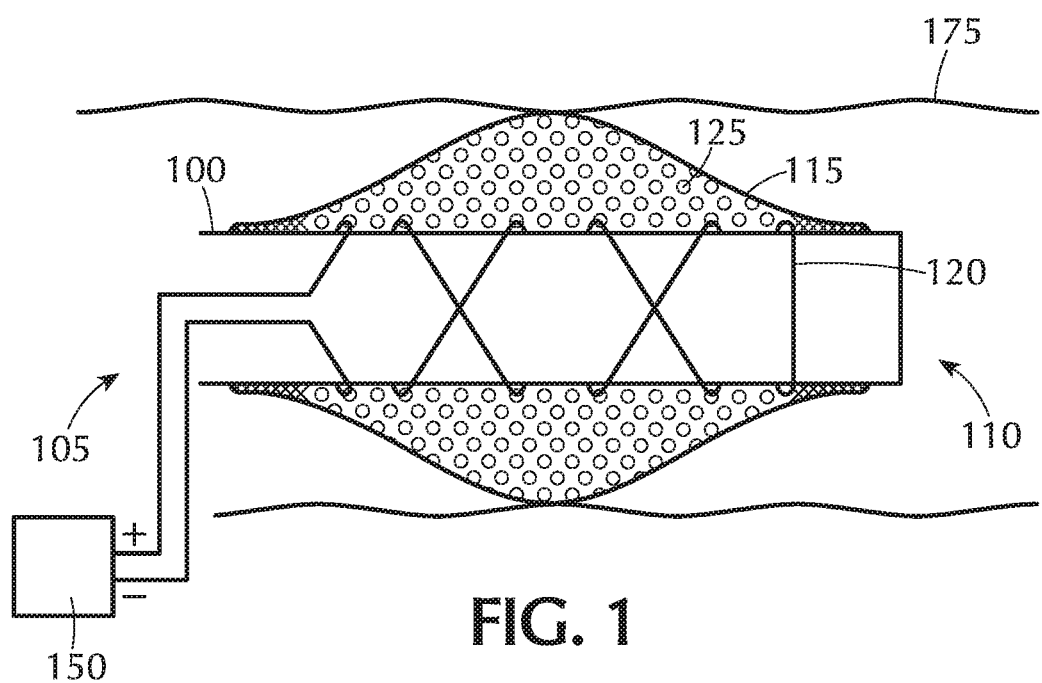
FIG. 1
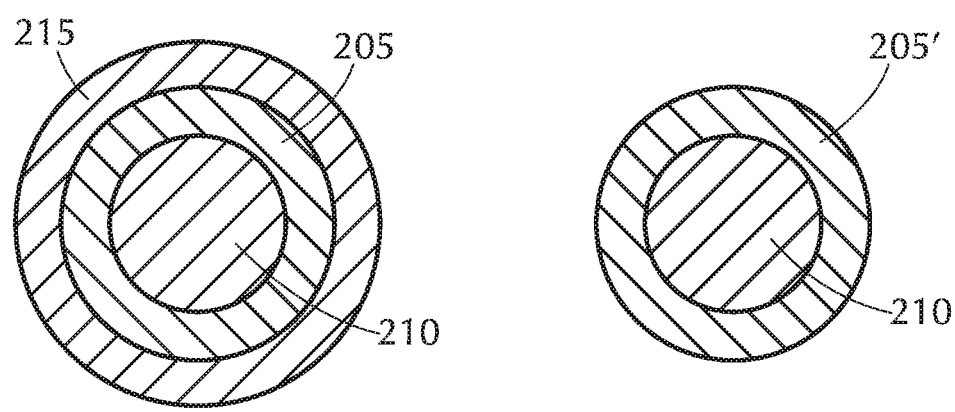
FIG. 2A
FIG. 2B

BALLOON GUIDE CATHETER WITH THERMALLY EXPANDABLE MATERIAL

CROSS-REFERENCE TO RELATED APPLICATIONS

This application claims the benefit of the following: U.S. Provisional Application No. 62/845,683, filed on May 9, 2019; U.S. Provisional Application No. 62/845,699, filed on May 9, 2019; U.S. Provisional Application No. 62/845,711, filed on May 9, 2019; and U.S. Provisional Application No. 62/845,747, filed on May 9, 2019, each of which is herein incorporated by reference in its entirety.

BACKGROUND OF THE INVENTION

Field of the Invention

The present invention relates to an intravascular medical system. In particular, the present invention is directed to an improved balloon guide catheter filled with thermally expandable material, rather than a pressurized liquid inflation media that must be dispensed/expelled in order to inflate/deflate, respectively, the balloon.

Description of Related Art

Catheters are widely used today in connection with a variety of intravascular medical procedures or treatments. One such widely adopted use or application of an intravascular catheter is in a thrombectomy medical procedure following an acute ischemic stroke (AIS) in which a sheath guide catheter (non-balloon guide catheter) or balloon guide catheter is introduced into the internal carotid artery to serve as a conduit for ancillary devices such as guidewire(s), microcatheter(s), stentriever(s) and intermediate catheter(s). The sheath guide catheter (non-balloon guide catheter) maintains access to the intended treatment location within a blood vessel and shortens procedural times by facilitating multiple passes with ancillary devices to the treatment location. Use of a balloon guide catheter provides the additional benefit, once inflated to an expanded state, of arresting blood flow and achieving complete apposition of the vessel. The blood flow arrest offers extra security in limiting the blood pressure exerted on the clot as well as maximizing the suction performance during the aspiration stage, as the stentriever and/or direct aspiration catheter retracts back into the balloon guide catheter with the captured clot. While such benefits are readily apparent and clinically proven, use of a balloon guide catheter requires somewhat arduous prepping steps be followed in ridding the inflating lumen and balloon of residual air to be replaced with a pressurized liquid inflating media. These prepping steps, performed prior to the introduction of the balloon guide catheter into the body, deter some physicians or interventionalists from using a balloon guide catheter altogether despite such advantages, instead choosing to employ a sheath guide catheter (non-balloon guide catheter) that doesn't require such prepping steps.

Prior to being introduced into the target vessel of the body, a conventional balloon guide catheter is prepped by the physician or interventionalist following a multi-step process to properly purge residual air trapped therein. This preparatory procedure typically calls for applying a vacuum or negative pressure at an inflation port to remove the residual air, followed immediately thereafter by dispensing of pressurized liquid inflation media back into the catheter. This step is repeated multiple times until no air is visible in the inflated balloon. If the purging steps are not followed correctly or skipped over entirely, the residual air in the balloon guide catheter may be exhausted into the blood vessel, in the event of a possible balloon failure, having a dangerous and harmful effect on the patient.

It is therefore desirable to eliminate the need for a pressurized liquid inflation media to purge the balloon guide catheter of residual air thereby increasing the desirability and ease of use of the device while optimizing time efficiency as well reducing safety risks.

SUMMARY OF THE INVENTION

An aspect of the present invention is directed to an improved balloon catheter that eliminates the need for pressurized liquid inflation media to be dispensed/expelled in order to inflate/deflate, respectively, the balloon.

Another aspect of the present invention relates to an improved balloon catheter that substitutes thermally expandable material for the pressurized liquid inflation media to expand and contract the balloon.

Still another aspect of the present invention relates to an improved balloon catheter that eliminates the need for inflation/deflation lumen thereby maximizing the inner diameter of the catheter.

While still another aspect of the present invention is directed to a balloon catheter including a heating element disposed about a portion of an outer surface of a catheter shaft. A balloon is mounted about the outer surface of the catheter shaft to coincide with the heating element. Thermally expandable material is disposed inside the mounted balloon.

Yet another aspect of the present invention relates to a method for using in a medical procedure in a vessel the balloon catheter described in the preceding paragraph. The method including the steps of, while the thermally expandable material is in a thermally compressed state with the balloon having a reduced outer diameter, advancing the balloon catheter through the vessel to a target site. Thereafter, applying an electrical signal to the heating element generating heat causing the thermally expandable material to automatically expand and enlarge the outer diameter of the balloon occluding blood flow in a distal direction beyond the enlarged balloon.

While still another aspect of the present invention is directed to a method of manufacture of an assembled balloon catheter. A catheter shaft is provided having a proximal end, an opposite distal end and an outer surface. About a portion of the outer surface of the catheter a heating element is wrapped. Then, a balloon is positioned about the catheter shaft to coincide with the heating element. A volume defined between an inner surface of the balloon and the outer surface of the catheter shaft is then filled with thermally expandable material. Lastly, the balloon is mounted to the outer surface of the catheter shaft encapsulating therein the thermally expandable material while in the compressed state.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which:

FIG. 1 depicts the present inventive balloon catheter in which the balloon is filled with thermally expandable microspheres, wherein the microspheres are illustrated in a thermally expanded state enlarging the outer diameter of the balloon (expanded state);

FIG. 2A is a cross-sectional view of a single exemplary thermally expandable microsphere;

FIG. 2B is a cross-sectional view of another exemplary thermally expandable microsphere;

DETAILED DESCRIPTION OF THE INVENTION

Figure 3:
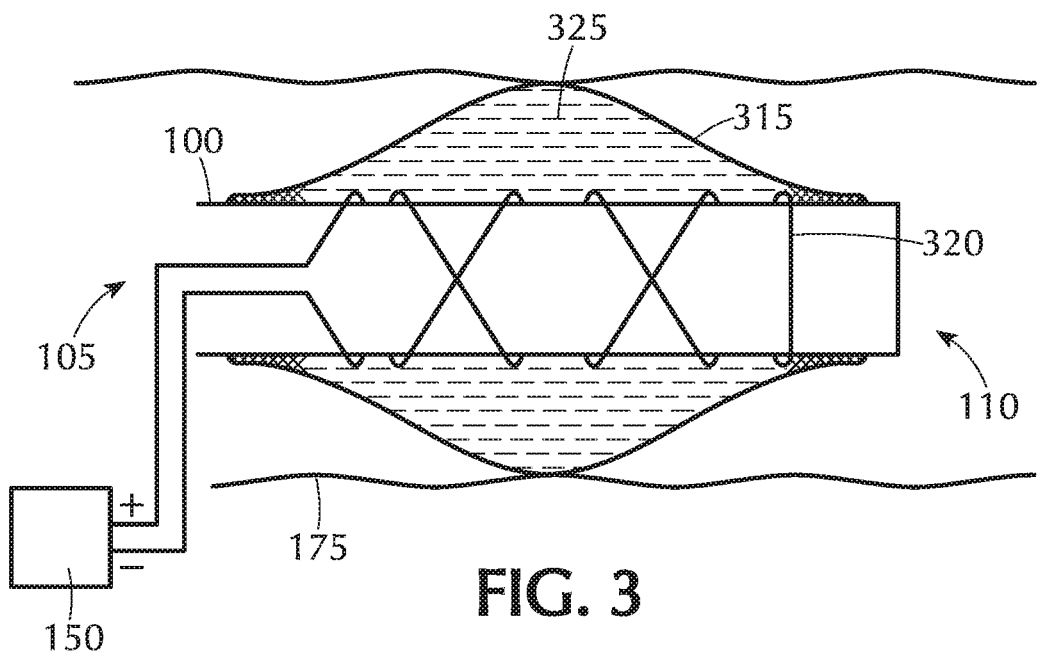
FIG. 3 depicts the present inventive balloon catheter in which the balloon is filled with a thermally expandable liquid or gel, wherein the liquid or gel is illustrated in a thermally expanded state enlarging the outer diameter of the balloon (expanded state)

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionalist. The terms "occlusion", "clot" or "blockage" are used interchangeably.

The present inventive balloon catheter eliminates altogether the need for a pressurized liquid inflation media (typically, a 50% contrast saline solution) to be dispensed/expelled in order to inflate/deflate, respectively, the balloon. Instead, at the time of manufacture the balloon is filed with a thermally expandable material (e.g., thermally expandable liquid(s), thermally expandable solid(s) or any combination thereof) while in a thermally compressed (non-expanded) state that need not be exhausted/removed/expelled from the catheter thereafter. Referring to FIG. 1, the balloon catheter in accordance with the present invention includes a catheter shaft or body 100 having a proximal end 105 and an opposite distal end 110. A heating element 120 is disposed about a portion of the outer surface of the catheter shaft or body 100 that coincides with a balloon 115 mounted proximate the distal end 110 of the catheter shaft 100. The heating element 120 in FIG. 1 is a wire, coil, strip or ribbon of electrically conductive material such as tungsten, platinum, nickel, titanium, nitinol or stainless steel. Electrical wires or leads electrically connect the heating element 120 to a power supply 150 providing electrical energy exciting the heating wire thereby producing or generating heat. In the exemplary embodiment depicted in FIG. 1 the heating coil 120 is crisscrossed, but other configurations of the wrapping of the heating coil about the outer surface of the catheter shaft are contemplated and within the intended scope of the present invention. Where the heating coil is crisscrossed, the coil is insulated to prevent an electrical short from occurring.

Rather than being inflated or filled with a pressurized liquid inflation media that must later be expelled or purged via an inflation/deflation lumen during prepping of the catheter prior to introduction into the body, the balloon 115 of the present inventive catheter during manufacture is filled with a thermally expandable material such as thermally expandable liquids, thermally expandable solids or any combination thereof. Once the thermally expandable material, while in a compressed (non-expanded) state, has been introduced into the balloon, thereafter in order to transition the balloon back to its compressed/reduced/non-expanded state the thermally expandable material need not be removed, dispensed or purged from the catheter. Rather, the thermally expandable material automatically returns to its original compressed state (non-expanded state) upon removal or withdrawal of the heat. Typically, the thermally expandable material is a thermally expandable particle or microsphere. Furthermore, the thermally expandable solid may serve a dual purpose of heating coil and expandable material, wherein a stent (e.g., stent shaped like a sinusoidal wave pattern) is employed to facilitate greater expansion, as described in greater detail below.

FIG. 2A is a cross-sectional view of a single exemplary thermally expandable microsphere 125 that comprises an outer polymer shell such as thermoplastic resin 205 having a relatively low glass transition temperature (Tg) and a gas blowing agent (pressurized gas inner core) 210 encapsulated therein. The relatively low glass transition temperature may be in the range of approximately 45° C. to approximately 100° C., preferably in the range of approximately 45° C. to approximately 65° C., more preferably in the range of approximately 45° C. to approximately 55° C. The gas blowing agent 210 may include hydrocarbons, pentane 1 or other gases. When the outer polymer shell 205 is heated above its glass transition temperature (Tg), the pressurized gas inner core 210 forces the outer polymer shell 205 to expand. The outer polymer shell 205 itself may also be encapsulated with an outer elastomeric shell 215 (e.g., thermoplastic polyurethane (TPU)) such that the outer elastomeric shell 215 compresses the thermoplastic shell 205 to recompress the contained pressurized gas 210 upon removal of heat from the heating element or source, the thermoplastic shell 205 having a memory to revert to its original smaller/reduced size when its temperature is lowered to a point below its softening point. An alternative configuration is depicted in FIG. 2B wherein the outer polymer shell is formed of a single elastomeric shell 205' (e.g., thermoplastic polyurethane (TPU), styrene-ethylene-butylene-styrene (SEBS) or other elastomers) such that when heated above a softening point, the compressed gas inner core 210 expands the elastomeric shell 205' to inflate the balloon. It is advantageous to supply the thermally expanding pressurized gas contained in numerous microspheres to limit exposure to gas leakage in the event of a failure if the gas was supplied in a single larger sphere or balloon. Each of the microspheres may range from approximately 0.01 μm to approximately 0.1 μm, preferably from approximately 0.01 μm to approximately 0.05 μm, more preferably from approximately 0.01 μm to approximately 0.025 μm.

During manufacture, the heating coil 120 is wrapped about a portion of the outer surface of the catheter shaft 100 that coincides with the positioning of the balloon 115 to be mounted thereafter to the outer surface of the catheter shaft. In the exemplary embodiment shown in FIG. 1, the heating coil 120 is wrapped in a crisscross configuration but other arrangements or designs are contemplated and within the intended scope of the present invention. As the balloon is being mounted to the outer surface of the catheter shaft during manufacture, the volume between the balloon 115 and catheter shaft 100 is filled with thermally expandable material 125, while the thermally expandable material is in a compressed (non-expanded) state. After being filed with the thermally expandable material 125, the balloon 115 is then mounted, bonded, welded or otherwise secured to the outer surface of the catheter shaft 100 using conventional techniques. Once assembled, the balloon catheter comprises the heating coil 120 disposed between the outer surface of the catheter shaft 100 and the inner surface of the balloon 115. The mounted balloon may be tightly wrapped about the outer surface of the catheter shaft for minimizing profile delivery or alternatively, a pliable and/or loose balloon may be utilized such that when the thermally expandable material is in its compressed (non-expanded) state, the balloon is free to contort in an atraumatic manner as it is being advanced through tortuous vasculature and when the thermally expandable material is in its expanded state, the balloon becomes taught to fully oppose the vessel and arrest blood flow. Furthermore, the thermally expandable material disposed inside the balloon during manufacture or assembly is contained therein, never being removed from nor more added to the balloon thereafter. That is, at no time during prepping or thereafter introduction of the catheter in the body is anything introduced into or purged from inside the balloon. The assembled balloon catheter is introduced into the vessel while the thermally expandable material is in a compressed (non-expanded) state so that the balloon has a minimum outer diameter advanceable through the vessel to the target site in the body.

Figure 4:
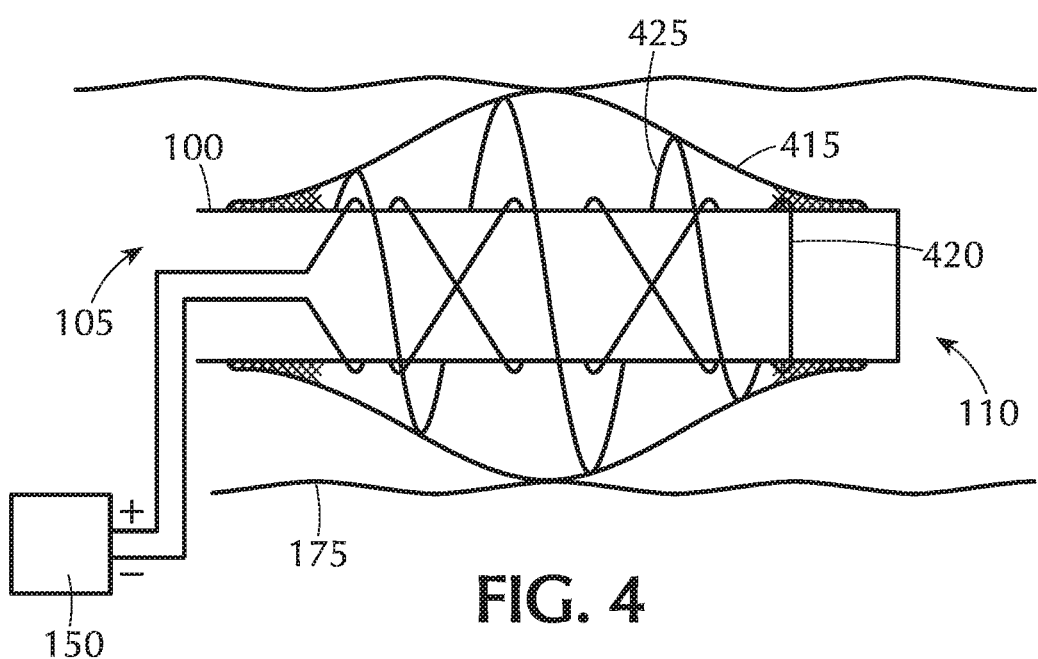
FIG. 4 depicts the present inventive balloon catheter in which a thermally expansive conductive structure (e.g., a conductive stent) is disposed within the balloon, wherein the thermally expansive conductive structure is illustrated in a thermally expanded state enlarging the outer diameter of the balloon (expanded state)
Figure 5:
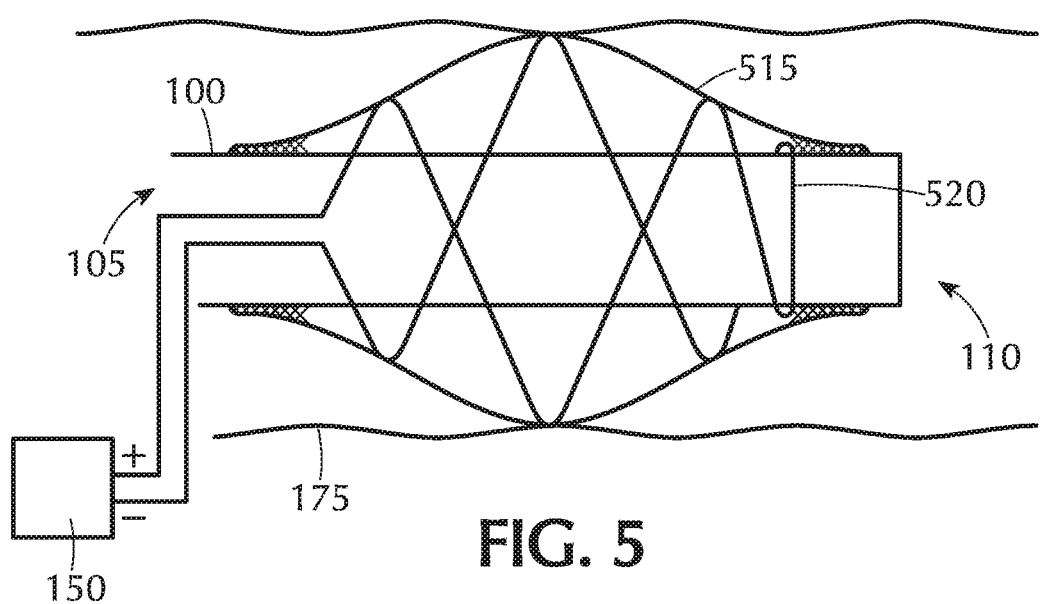
FIG. 5 depicts the present inventive balloon catheter in which the heating coil that coincides with the balloon is formed from a shape memory metal (e.g., Nitinol), wherein the heat generated by the coil causes the heating coil material to revert to a pre-set shape having a larger diameter than the compressed balloon which expands or increases the outer diameter of the balloon to the expanded state illustrated.

Upon reaching the target site in the vessel, an electrical signal generated by the power source 150 is applied to the heating coil 120 generating heat which radiates outward. The heat produced by the heating element 120 causes the thermally expandable material such as a thermoplastic outer shell 205 of the thermally expandable microspheres 125 to soften and expand under pressure of the inner core 210 thereby expanding the outer diameter of the thermally expandable microspheres which, in turn, expands or increases the outer diameter of the balloon 115. Alternatively, heat produced by the heating coil 320 causes a thermally expandable liquid or gel 325 to expand in volume which, in turn, expands or increases the outer diameter of the balloon 315, as shown in FIG. 3. In another embodiment illustrated in FIG. 4, the heat produced by the heating coil 420 causes a metallic stent like frame 425 disposed within the balloon to expand which, in turn, expands or increases the outer diameter of the balloon 415. In yet another embodiment, the heating coil 520 itself is formed from a shape memory metal with high impedance, such as Nitinol, and the heat generated from the heating coil causes the heating coil to revert to a shape previously set through conventional shape setting techniques, the pre-set shape having a larger diameter than the compressed balloon which expands or increases the outer diameter of the balloon 515. Where a taught elastic balloon is incorporated into the catheter, the force exerted by the expandable material is greater than the force required to stretch the biased closed balloon to an expanded state. In its expanded state, the outer walls of the balloon physically contact the inner walls of the vessel occluding blood flow distally beyond the inflated balloon. Prior to withdrawal of the balloon catheter from the body, the electrical signal provided by the power source to the heating element is cut off allowing the thermally expandable material to cool/reduce/lower in temperature and automatically compress (reduce in outer diameter) allowing the balloon, in turn, to reduce in outer diameter as well. Upon the balloon returning to its compressed (non-expanded) state, the balloon may be easily removed in a proximal direction from the body.

Numerous advantages are provided with the current configuration of the balloon catheter, some of which are discussed in detail below. The thermally expandable material(s) are dispensed into the balloon at the time of manufacture/assembly of the catheter and thereafter remain in the balloon at all times thereafter.

Accordingly, the need for both an inflation lumen and/or exhaust lumen defined in the catheter shaft of conventional balloon catheters for inflating the balloon using a pressurized liquid inflation media and thereafter exhausting the pressurized liquid inflation media in order to deflate the balloon prior to removal from the body has been eliminated. Since the need for an inflation/deflation lumen has been eliminated, the inner diameter may be maximizable to accommodate ancillary devices having a larger diameter. Still another benefit is that residual air need not be purged from the balloon itself thereby reducing prepping time making the device simpler and more desirable to use. Yet another advantage is that the conductive heating wire may serve the dual function of reinforcing the catheter shaft. Arranging the conductive heating wire in or as part of a braid, coil, or longitudinal brace pattern enhances the kink resistance, pushability and torqueability of the catheter shaft providing optimized and varied stiffness anywhere axially along the catheter from its proximal end to its distal end.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A balloon catheter comprising:
   a catheter shaft having a proximal end, an opposite distal end and an outer surface;
   a heating element disposed about a portion of the outer surface of the catheter shaft;
   a balloon mounted about the outer surface of the catheter shaft to coincide with the heating element; and
   thermally expandable material disposed inside the mounted balloon;
   wherein the balloon along both proximal and distal ends thereof is secured about the outer surface of the catheter shaft defining a volume therebetween in which the thermally expandable material is encapsulated.

2. The balloon catheter according to claim 1, wherein the thermally expandable material is a thermally expandable solid, a thermally expandable liquid or a combination thereof.

3. The balloon catheter according to claim 2, wherein the thermally expandable material is microspheres or particles.

4. The balloon catheter according to claim 2, wherein the thermally expandable material is a thermally expandable liquid, a thermally expandable gel or a combination thereof.

5. The balloon catheter according to claim 2, wherein the thermally expandable material is a conductive stent.

6. The balloon catheter according to claim 2, wherein the heating element itself is the thermally expandable material.

7. The balloon catheter according to claim 3, wherein the microspheres have a thermoplastic shell encapsulating a pressurized blowing agent.

8. The balloon catheter according to claim 7, wherein an outer elastomeric shell surrounds the thermoplastic shell.

9. The balloon catheter according to claim 3, wherein the microspheres have an elastomeric shell encapsulating a pressurized blowing agent.

10. The balloon catheter according to claim 1, wherein the catheter shaft has no inflation lumen and no deflation lumen.

11. A method for using a balloon catheter in a medical procedure in a vessel, wherein the balloon catheter includes: a catheter shaft having a proximal end, an opposite distal end and an outer surface; a heating element disposed about a portion of the outer surface of the catheter shaft; a balloon mounted about the outer surface of the catheter shaft proximate the distal end; the balloon arranged along the catheter shaft to coincide with the heating element; and thermally expandable material disposed inside the mounted balloon; wherein the balloon along both proximal and distal ends thereof is secured about the outer surface of the catheter shaft defining a volume therebetween in which the thermally expandable material is encapsulated; the method comprising the steps of:
    while the thermally expandable material is in a thermally compressed state with the balloon having a reduced outer diameter, advancing the balloon catheter through the vessel to a target site;
    applying an electrical signal to the heating element generating heat causing the thermally expandable material to automatically expand and enlarge the outer diameter of the balloon occluding blood flow in a distal direction beyond the enlarged balloon.

12. The method according to claim 11, wherein the thermally expandable material is a thermally expandable solid, a thermally expandable liquid or a combination thereof.

13. The method according to claim 12, wherein the thermally expandable material is microspheres or particles; and upon application of the electrical signal an outer shell softens and expands under pressure of a pressurized blowing agent encapsulated therein enlarging the microspheres or particles in size causing the balloon to enlarge.

14. The method according to claim 12, wherein the thermally expandable material is a thermally expandable liquid, a thermally expandable gel or a combination thereof.

15. The method according to claim 12, wherein the thermally expandable material is a conductive stent.

16. The method according to claim 12, wherein the heating element itself is the thermally expandable material.

17. The method according to claim 11, further comprising the steps of:
    cutting off the electrical signal to the heating element and allowing the thermally expandable material to cool to a compressed state and reducing the outer diameter of the balloon; and
    withdrawing of the balloon catheter from the vessel in a proximal direction while the outer diameter of the balloon is reduced.

18. The method according to claim 11, wherein during use of the balloon catheter the thermally expandable material is not dispensed from the catheter to reduce in size the balloon.

19. A method of manufacture of an assembled balloon catheter, comprising the steps of:
    providing a catheter shaft having a proximal end, an opposite distal end and an outer surface;
    wrapping a heating element about a portion of the outer surface of the catheter shaft;
    positioning a balloon about the outer surface of the catheter shaft to coincide with the heating element;
    filling a volume defined between an inner surface of the balloon and the outer surface of the catheter shaft with thermally expandable material, while the thermally expandable material is in a compressed state; wherein the balloon along both proximal and distal ends thereof is secured about the outer surface of the catheter shaft defining the volume therebetween in which the thermally expandable material is encapsulated; and
    mounting the balloon to the outer surface of the catheter shaft containing therein the thermally expandable material while the thermally expandable material is in the compressed state.

* * * * *